United States Patent
Gordon et al.

(10) Patent No.: US 9,422,207 B2
(45) Date of Patent: Aug. 23, 2016

(54) COMPOUNDS AND METHODS FOR THE PRODUCTION OF LONG CHAIN HYDROCARBONS FROM BIOLOGICAL SOURCES

(75) Inventors: John Cameron Gordon, Los Alamos, NM (US); Louis A. Silks, Los Alamos, NM (US); Andrew D. Sutton, Los Alamos, NM (US); Ruilian Wu, Los Alamos, NM (US); Marcel Schlaf, Ontario (CA); Fraser Waldie, Alberta (CA); Ryan West, West Chester, OH (US); Dimitris Ioannis Collias, Mason, OH (US)

(73) Assignees: Los Alamos National Security, LLC, Los Alamos, NM (US); The Proctor & Gamble Company, Cincinnati, OH (US)

( * ) Notice: Subject to any disclaimer, the term of this patent is extended or adjusted under 35 U.S.C. 154(b) by 0 days.

(21) Appl. No.: 14/344,178

(22) PCT Filed: Sep. 14, 2012

(86) PCT No.: PCT/US2012/055340
§ 371 (c)(1),
(2), (4) Date: Apr. 3, 2015

(87) PCT Pub. No.: WO2013/040311
PCT Pub. Date: Mar. 21, 2013

(65) Prior Publication Data
US 2015/0232394 A1    Aug. 20, 2015

Related U.S. Application Data

(60) Provisional application No. 61/534,496, filed on Sep. 14, 2011, provisional application No. 61/669,775, filed on Jul. 10, 2012.

(51) Int. Cl.
| | |
|---|---|
| *C07C 1/22* | (2006.01) |
| *C10L 1/04* | (2006.01) |
| *C07D 307/54* | (2006.01) |
| *C07D 307/46* | (2006.01) |

(52) U.S. Cl.
CPC ............... *C07C 1/22* (2013.01); *C07D 307/46* (2013.01); *C07D 307/54* (2013.01); *C10L 1/04* (2013.01); *C07C 2523/44* (2013.01); *C10L 2200/04* (2013.01)

(58) Field of Classification Search
CPC .... C07C 1/22; C07C 2523/44; C07D 307/46; C07D 307/54; C10L 1/04; C10L 2200/04
See application file for complete search history.

(56) References Cited

U.S. PATENT DOCUMENTS

| | | |
|---|---|---|
| 4,895,984 A | 1/1990 | Eggersdorfer et al. |
| 6,028,231 A | 2/2000 | Markert |
| 2008/0161288 A1 | 7/2008 | Boyle et al. |
| 2011/0065929 A1 | 3/2011 | Shimizu et al. |

FOREIGN PATENT DOCUMENTS

WO    WO 2013/040311    3/2013

OTHER PUBLICATIONS

Dedsuksophon, W., "Study of liquid alkanes production from biomass-derived carbohydrates by aldol-condensation and hydrogenation processes." Engineering Journal 14.4 (2010): 1-10.*
Piancatelli, G., "Cyclopentenone from furan: an unusual Marckwald reaction." Heterocycles 23.3 (1985): 667-670.*
[Database Registry Chemical Abstracts Service, Columbus, Ohio, Accession No. RN 1135274-36-0 , Entered STN: Apr. 16, 2009].*
Alamillo et al, "The Selective Hydrogenation of Biomass-Derived 5-Hydroxymethylfurfural Using Heterogeneous Catalysts", Green Chem., May 2012, 14(5), 1413-1419.
Dedsuksophon et al, Study of Liquid Alkanes Production From Biomass-Derived Carbohydrates by Aldol-Condensation and Hydrogenation Processes, Engineering Journal: 2010, 14(4), 1-10.
Huber et al, "Production of Liquid Alkanes by Aqueous-Phase Processing of Biomass-Derived Carbohydrates", Science, 308, Jun. 3, 2005, 1446-1450.
International Patent Application No. PCT/US12/55340: International Search Report and the Written Opinion dated Dec. 18, 2012, 18 pages.
Kobayashi et al, "Lanthanide Triflates as Water-Tolerant Lewis Acids. Activation of Commercial Formaldehyde Solution and Use in the Aldol Reaction of Silyl Enol Ethers with Aldehydes in Aqueous Media", Journal of Organic Chemistry, Jul. 1994, 59(13), 3590-3596.
Li et al, "Upgrading of Low-Boiling Fraction of Bio-Oil in Supercritical Methanol and Reaction Network", Bioresource Technology, 2011, 102, 4884-4889, Published Online: Jan. 22, 2011,.
Michels et al, "Virial Coefficients of Hydrogen and Deuterium At Temperatures Between -175° C and +150° C. Conclusions From the Second Virial Coefficient With Regards to the Intermolecular Potential", Physica, Jun. 1960, 26(6), 393-408.

(Continued)

*Primary Examiner* — Samantha Shterengarts
*Assistant Examiner* — Matt Mauro
(74) *Attorney, Agent, or Firm* — Lewis Roca Rothgerber Christie LLP

(57) ABSTRACT

The present invention is directed to the preparation of oxygenated, unsaturated hydrocarbon compounds, such as derivatives of furfural or hydroxymethyl furfural produced by aldol condensation with a ketone or a ketoester, as well as methods of deoxidatively reducing those compounds with hydrogen under acidic conditions to provide saturated hydrocarbons useful as fuels.

38 Claims, No Drawings

(56) References Cited

OTHER PUBLICATIONS

Misra, A.K. and Agnihotri, G., "Preparation of Polyhydroxyalkyl- and C-glycosylfuran Derivatives From Free Sugars Catalyzed by Cerium(III) Chloride in Aqueous Solution: An Improvement of the Garcia Gonzalez Reaction" Carbohydrate Research, May 17, 2004, 2004, 339(7), 1381-1387.

Nakagawa, Y. and Tomishige, K., "Total Hydrogenation of Furan Derivatives Over Silica-Supported Ni-Pd Alloy Catalyst", Catalysis Communications, Nov. 2010, 12(3),154-156.

Rodrigues et al, "A Convenient, One-Step, Synthesis of α-C-Glycosidic Ketones in Aqueous Media", Chemical Communications, Oct. 2, 2000, 2049-2050.

Schiavo et al, "Hydrogenation Catalytique du 5-hydrocymentylfurfural en Milieu Aqueux", Bulletin de la Societe Chimique de France, 1991, 5, 704-711, Pagel-English summary.

Waidmann et al, "Functional Group Dependence of the Acid Catalyzed Ring Opening of Biomass Derived Furan Rings: An Experimental and Theoretical Study", Catalysis Science Technology, Jan. 2013, 3(1), 106-115.

* cited by examiner

COMPOUNDS AND METHODS FOR THE PRODUCTION OF LONG CHAIN HYDROCARBONS FROM BIOLOGICAL SOURCES

CROSS-REFERENCE TO RELATED APPLICATIONS

This application is the National Stage of International Application No. PCT/US2012/055340, filed Sep. 14, 2012, which claims the benefit of U.S. Provisional Application No. 61/534,496, filed Sep. 14, 2011 and U.S. Provisional Application No. 61/669,775, filed Jul. 10, 2012, the entireties of which are incorporated herein by reference.

GOVERNMENT RIGHTS

The United States government has rights in this invention pursuant to Contract No. DE-AC52-06NA25396 between the United States Department of Energy and Los Alamos National Security, LLC for the operation of Los Alamos National Laboratory.

TECHNICAL FIELD

The present invention is directed to the preparation of oxygenated, unsaturated hydrocarbon compounds, as well as methods of deoxidatively reducing those compounds to provide saturated hydrocarbons useful as fuels and chemical feedstocks.

BACKGROUND

Saturated hydrocarbons containing from about seven to about fifteen carbons, up to about twenty-six carbons are used as fuel, and other materials. Such hydrocarbons are typically extracted or generated from petroleum, a non-renewable resource. Methods of generating fuel- and high-quality hydrocarbons from renewable sources are thus needed.

SUMMARY

The present invention is directed to methods of making compounds of formula I:

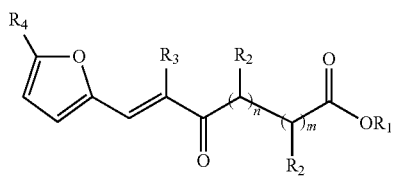

wherein $R_1$ is H or $C_{1-6}$alkyl; each $R_2$ is independently hydrogen or $C_{1-6}$alkyl; $R_3$ is H or $C_{1-6}$alkyl; $R_4$ is H, $C_{1-6}$alkyl, or substituted $C_{1-6}$alkyl; n is 1, 2, 3, or 4; and m is 1, 2, 3, or 4; comprising reacting a compound of formula A

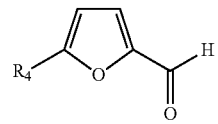

with a compound of formula B

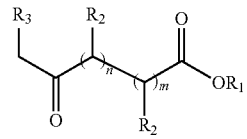

in the presence of a catalyst, for a time and at a temperature sufficient to provide the compound of formula I. Compounds of formula I, as well as methods of deoxidatively reducing compounds of formula I to produce hydrocarbon fuels, are also described.

The invention is also directed to methods of making compounds of formula II:

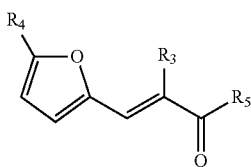

wherein $R_3$ is H or $C_{1-6}$alkyl; $R_4$ is H, $C_{1-6}$alkyl, or substituted $C_{1-6}$alkyl; and $R_5$ is $C_{1-16}$alkyl; comprising reacting a compound of formula A

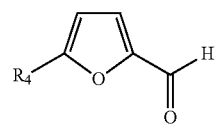

with a compound of formula C

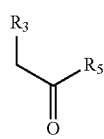

in the presence of catalyst, for a time and at a temperature sufficient to provide the compound of formula II. Compounds of formula II, as well as methods for deoxidatively reducing compounds of formula II to produce hydrocarbon fuels, are also described.

The invention is also directed to methods of converting oxygenated, unsaturated hydrocarbons to saturated hydrocarbons, in particular, hydrocarbon fuels, comprising reacting the oxygenated, unsaturated hydrocarbons with hydrogen under acidic conditions in the presence of a catalyst and a Lewis acid for a time and at a temperature sufficient to provide the saturated hydrocarbon.

DETAILED DESCRIPTION OF ILLUSTRATIVE EMBODIMENTS

It has heretofore been discovered that oxygenated biorenewable feedstocks obtained from mono-, di-, or polysaccharides can be used to generate fuel- and high-quality saturated hydrocarbons using an aldol reaction to generate an oxygenated unsaturated hydrocarbon that can be deoxidatively reduced to generate the fuel- and high-quality saturated hydrocarbons. Bioderived compounds useful in the present invention include, for example, 2, 3, 4, 5, and 6 carbon-containing compounds, for example hydroxymethyl furfural, furfural, methyl furfural, ethyl levulinate, homo ethyl levinate, and decan-2-one.

The aldol reaction is known per se in the art and involves the reaction of an aldehyde-containing compound with a ketone-containing compound to form an α,β-unsaturated ketone-containing compound:

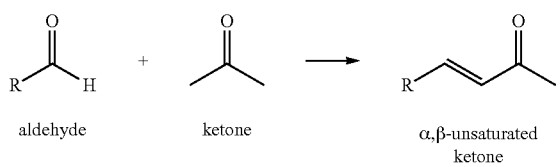

aldehyde     ketone     α,β-unsaturated ketone

It has now been discovered that the aldol reaction can be exploited to produce compounds having from seven to fifteen carbons using starting materials derived from saccharides, which are renewable resources. The resulting aldol products can then be deoxidatively reduced to produce the corresponding seven to fifteen carbon saturated hydrocarbons, which are useful as fuels, for example.

One embodiment of the invention is directed to methods of making compounds of formula I:

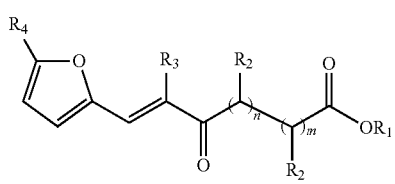

I wherein
$R_1$ is H or $C_{1-6}$alkyl;
each $R_2$ is independently hydrogen or $C_{1-6}$alkyl;
$R_3$ is H or $C_{1-6}$alkyl;
$R_4$ is H, $C_{1-6}$alkyl, or substituted $C_{1-6}$alkyl;
n is 1, 2, 3, or 4; and
m is 1, 2, 3, or 4; comprising:
reacting a compound of formula A

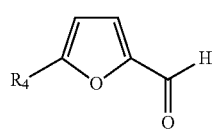

A with a compound of formula B

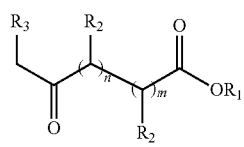

B in the presence of catalyst, for a time and at a temperature sufficient to provide the compound of formula I.

In preferred embodiments, the catalyst is a pyrrolidinium salt, preferably pyrrolidinium acetate.

The skilled person can readily determine an appropriate temperature for the described methods of making compounds of formula I, nevertheless, temperatures from about ambient temperature to about 200° C. are preferred, with ambient temperature being most preferred.

The skilled person can readily determine an appropriate time for the methods of making compounds of formula I, nevertheless, reaction times of from about 1 hour to about 48 hours are preferred. More preferred are reaction times of from about 6 hours to about 48 hours. Even more preferred are reaction times of from about 6 hours to about 24 hours.

The described methods are preferably performed in the absence of solvent, that is "neat." Solvents can be employed, however. Preferred solvents include tetrahydrofuran, ethyl acetate, alkyl alcohols, for example, methanol, ethanol, propanol, isopropanol, butanol, and the like, diethyl ether, methylene chloride, water, or a combination thereof.

It is also preferred that the methods be performed wherein neither the compound of formula A nor the compound of formula B is in excess. That is, in a preferred embodiment, the molar ratio of the compound of formula A to the compound of formula B is about 1:1.

In preferred embodiments, $R_1$ is $C_{1-4}$alkyl. In other preferred embodiments, $R_1$ is $C_{1-3}$alkyl. In other preferred embodiments, $R_1$ is methyl or ethyl. In other embodiments, $R_1$ is H.

In preferred embodiments, $R_2$ is H. In other preferred embodiments, $R_2$ is $C_{1-4}$alkyl. In other preferred embodiments, $R_2$ is $C_{1-3}$alkyl. In yet other embodiments, $R_2$ is $C_{1-2}$alkyl. In still other embodiments, $R_2$ is methyl.

In preferred embodiments, $R_4$ is hydrogen. In other embodiments, $R_4$ is $C_{1-4}$alkyl. In other preferred embodiments, $R_4$ is $C_{1-3}$alkyl. In yet other embodiments, $R_4$ is $C_{1-2}$alkyl. In still other embodiments, $R_4$ is methyl. In other embodiments, $R_4$ is substituted $C_{1-6}$alkyl. In such embodiments, it is preferably that $R_4$ is $C_{1-6}$alkyl substituted with —OH. Preferably, $R_4$ is —CH$_2$—OH. Also preferred is where $R_4$ is —CH$_2$—CH$_2$—OH. $R_4$ can also be $C_{1-6}$alkyl substituted with oxo or —COOH.

In preferred embodiments, n is 1, 2, or 3. In other embodiments, n is 1. In yet other embodiments, n is 2. In still other embodiments, n is 3.

In preferred embodiments, m is 1, 2, or 3. In other embodiments, m is 1. In yet other embodiments, m is 2. In still other embodiments, m is 3.

In preferred embodiments, the compound of formula A is

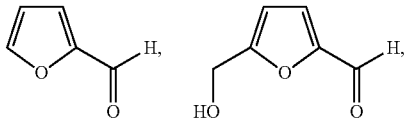

-continued

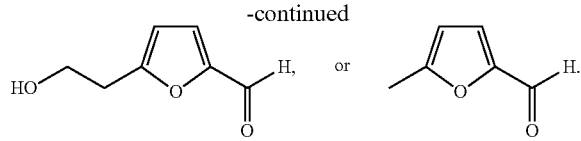

Preferably, the compound of formula B is

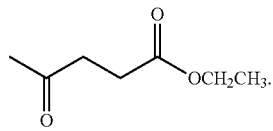

Also preferred is where the compound of formula B is

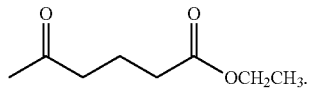

Also within the scope of the invention is conversion of the compounds of formula I to the corresponding saturated hydrocarbon using deoxidative reducing conditions. The deoxidative reducing conditions can either be according to the methods described herein or can be according to methods known to those skilled in the art.

Compounds of formula I are also within the scope of the invention:

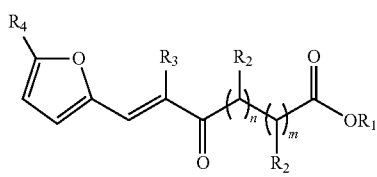

I wherein
$R_1$ is H or $C_{1-6}$alkyl;
each $R_2$ is independently hydrogen or $C_{1-6}$alkyl;
$R_3$ is H or $C_{1-6}$alkyl;
$R_4$ is H, $C_{1-6}$alkyl, or substituted $C_{1-6}$alkyl;
n is 1, 2, 3, or 4; and
m is 1, 2, 3, or 4;
with the proviso that when $R_1$ is H, $R_4$ is $C_{1-6}$alkyl or substituted $C_{1-6}$alkyl.

In preferred embodiments of compounds of formula I, $R_1$ is $C_{1-4}$alkyl. In other preferred embodiments, $R_1$ is $C_{1-3}$alkyl. In other preferred embodiments, $R_1$ is methyl or ethyl. IN still other embodiments, $R_1$ is H.

In preferred embodiments of compounds of formula I, $R_2$ is H. In other preferred embodiments, $R_2$ is $C_{1-4}$alkyl. In other preferred embodiments, $R_2$ is $C_{1-3}$alkyl. In yet other embodiments, $R_2$ is $C_{1-2}$alkyl. In still other embodiments, $R_2$ is methyl.

In preferred embodiments of compounds of formula I, $R_4$ is hydrogen. In other embodiments, $R_4$ is $C_{1-4}$alkyl. In other preferred embodiments, $R_4$ is $C_{1-3}$alkyl. In yet other embodiments, $R_4$ is $C_{1-2}$alkyl. In still other embodiments, $R_4$ is methyl. In other embodiments, $R_4$ is substituted $C_{1-6}$alkyl. In such embodiments, it is preferably that $R_4$ is $C_{1-6}$alkyl substituted with —OH. Preferably, $R_4$ is —CH$_2$—OH. Also preferred is where $R_4$ is —CH$_2$—CH$_2$—OH. $R_4$ can also be $C_{1-6}$alkyl substituted with oxo or —COOH.

In preferred embodiments of compounds of formula I, n is 1, 2, or 3. In other embodiments, n is 1. In yet other embodiments, n is 2. In still other embodiments, n is 3.

In preferred embodiments of compounds of formula I, m is 1, 2, or 3. In other embodiments, m is 1. In yet other embodiments, m is 2. In still other embodiments, m is 3.

Compounds of formula I are useful in the production of the corresponding saturated hydrocarbons. Compounds of formula I can be converted to the corresponding saturated hydrocarbon, preferably a fuel, using deoxidative reducing conditions. The deoxidative reducing conditions can either be according to the methods described herein or can be according to methods known to those skilled in the art.

Also within the scope of the invention are methods for converting compounds of formula I

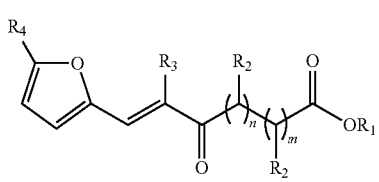

I wherein
$R_1$ is H or $C_{1-6}$alkyl;
each $R_2$ is independently hydrogen or $C_{1-6}$alkyl;
$R_3$ is H or $C_{1-6}$alkyl;
$R_4$ is H, $C_{1-6}$alkyl, or substituted $C_{1-6}$alkyl;
n is 1, 2, 3, or 4; and
m is 1, 2, 3, or 4;

to fuels, which are preferably the corresponding saturated hydrocarbons. These methods comprise deoxidatively reducing the compound of formula I, preferably using hydrogenation conditions such as those described herein or known to those skilled in the art.

Methods of making compounds of formula II are also within the scope of the invention:

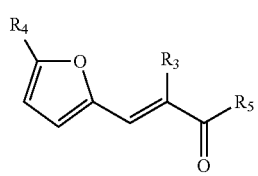

II wherein
R₃ is H or $C_{1-6}$alkyl;
R₄ is H, $C_{1-6}$alkyl, or substituted $C_{1-6}$alkyl; and
R₅ is $C_{1-16}$alkyl;
comprising:
reacting a compound of formula A

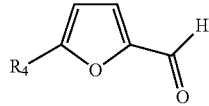

A with a compound of formula C

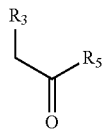

C in the presence of catalyst, for a time and at a temperature sufficient to provide the compound of formula II.

In preferred embodiments, the catalyst is a pyrrolidinium salt, preferable pyrrolidinium acetate.

The skilled person can readily determine an appropriate temperature for the described methods for making compounds of formula II, nevertheless, temperatures from about ambient temperature to about 200° C. are preferred, with ambient temperature being most preferred.

The skilled person can readily determine an appropriate time for the methods for making compounds of formula II, nevertheless, reaction times of from about 1 hour to about 48 hours are preferred. More preferred are reaction times of from about 6 hours to about 48 hours. Even more preferred are reaction times of from about 6 hours to about 24 hours.

The method is preferably performed in the absence of solvent, that is "neat." Solvents can be employed, however. Preferred solvents include tetrahydrofuran, ethyl acetate, alkyl alcohols, for example, methanol, ethanol, propanol, isopropanol, butanol, and the like, diethyl ether, methylene chloride, water, or a combination thereof.

It is also preferred that the methods for making compounds of formula II be performed wherein neither the compound of formula A nor the compound of formula C is in excess. That is, in a preferred embodiment, the molar ratio of the compound of formula A to the compound of formula C about 1:1.

In preferred embodiments, R₄ is hydrogen. In other embodiments, R₄ is $C_{1-4}$ alkyl. In other preferred embodiments, R₄ is $C_{1-3}$alkyl. In yet other embodiments, R₄ is $C_{1-2}$alkyl. In still other embodiments, R₄ is methyl. In other embodiments, R₄ is substituted $C_{1-6}$alkyl. In such embodiments, it is preferably that R₄ is $C_{1-6}$alkyl substituted with —OH. Preferably, R₄ is —CH₂—OH. Also preferred is where R₄ is —CH₂—CH₂—OH. R₄ can also be $C_{1-6}$alkyl substituted with oxo or —COOH.

In preferred embodiments, R₅ is $C_{1-8}$ alkyl. In other preferred embodiments, R₅ is $C_{1-7}$alkyl. In other preferred embodiments, R₅ is $C_{1-6}$alkyl. In other preferred embodiments, R₅ is $C_{1-5}$alkyl. In other preferred embodiments, R₅ is $C_{1-4}$alkyl. In other preferred embodiments, R₅ is $C_{1-3}$alkyl. In other preferred embodiments, R₅ is $C_{1-2}$alkyl. In other preferred embodiments, R₅ is methyl.

In preferred embodiments, the compound of formula A is

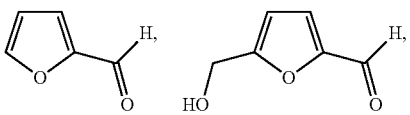

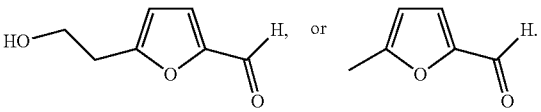

Preferably, the compound of formula C is

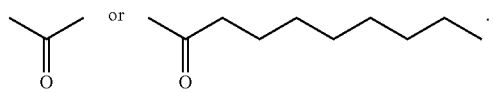

It is also within the scope of the invention that the compound of formula II be converted to the corresponding saturated hydrocarbon, that is, fuel, using deoxidative reducing conditions. The deoxidative reducing conditions can either be according to the methods described herein or can be according to methods known to those skilled in the art.

Also within the scope of the invention are methods of converting an oxygenated, unsaturated hydrocarbon or oxygenated, saturated hydrocarbon to a saturated hydrocarbon comprising reacting the oxygenated, unsaturated hydrocarbon or the oxygenated, saturated hydrocarbon with hydrogen under acidic conditions in the presence of a catalyst and a Lewis acid for a time and at a temperature sufficient to provide the saturated hydrocarbon.

The oxygenated, unsaturated hydrocarbon or oxygenated, saturated hydrocarbon can be any oxygenated, unsaturated hydrocarbon or oxygenated, saturated hydrocarbon known in the art. Preferably, the oxygenated, unsaturated hydrocarbons of the invention include from 1 to 5 double bonds, preferably 1 to 4 double bonds, more preferably 1 to 3 double bonds. Oxygenated, unsaturated hydrocarbons within the scope of the invention can also have one or two double bonds.

"Oxygenated, saturated hydrocarbons," as used herein refers to compounds having no aromatic double bonds. Such compounds may include unsaturated, aromatic groups such as heterocycles, for example, furans.

The oxygenated, unsaturated hydrocarbon or oxygenated, saturated hydrocarbon can also have any number of oxygens, present in the compound as an ether, ketone, ester, or saturated or unsaturated heterocycle. Preferably, the oxygenated, unsaturated hydrocarbon or oxygenated, saturated hydrocarbon will have from 1 to 10 oxygen atoms, more preferably 1 to 8 oxygen atoms, even more preferably 1 to 6 oxygen atoms. Also preferred are compounds containing 1 to 4 oxygen atoms.

Preferred oxygenated, unsaturated hydrocarbons can be, for example, any of the oxygenated unsaturated hydrocarbons described herein or known in the art. Preferred oxygenated, unsaturated hydrocarbons include:

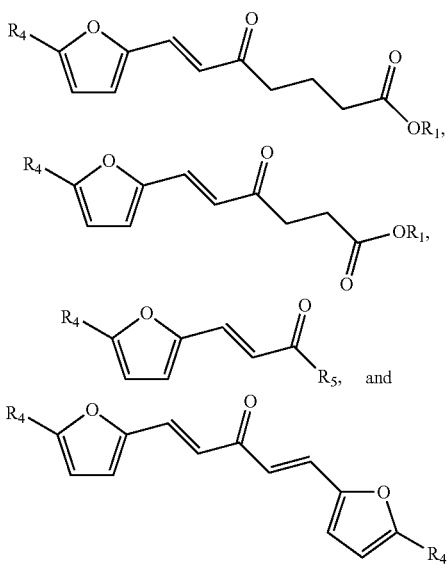

wherein
R₁ is H or $C_{1-6}$alkyl;
R₄ is H, $C_{1-6}$alkyl, or substituted $C_{1-6}$alkyl; and
R₅ is $C_{1-16}$alkyl.

Preferred oxygenated, saturated hydrocarbons can be, for example, any of the oxygenated saturated hydrocarbons described herein or known in the art. Preferred oxygenated, saturated hydrocarbons include:

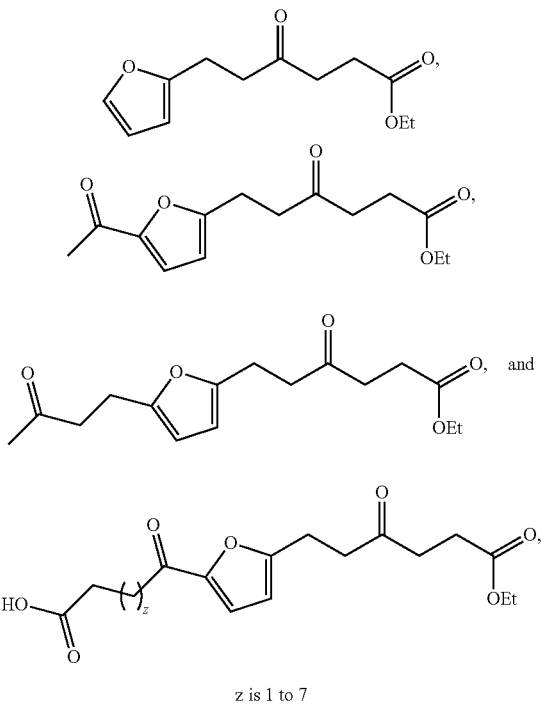

z is 1 to 7

Preferably, the methods for converting an oxygenated, unsaturated hydrocarbon or oxygenated, saturated hydrocarbon to a saturated hydrocarbon are performed under acidic conditions. Acidic conditions, known to those skilled in the art to have a pH of from less than 1 to less than 7, can be obtained using methods known to those skilled in the art. Preferably, the acidic conditions are obtained using a protic acid. Preferably, the protic acid is acetic acid, hydrochloric acid, nitric acid, formic acid, sulfuric acid, trifluoromethanesulfonic acid, and combinations thereof.

The hydrogen can be applied at either atmospheric pressure at pressures above atmospheric pressure. For example, preferred pressures of hydrogen are from about 15 psi to about 500 psi, with about 100 psi being most preferred.

Those skilled in the art can determine a suitable temperature for the methods for converting an oxygenated, unsaturated hydrocarbon or oxygenated, saturated hydrocarbon to a saturated hydrocarbon, however, temperatures of from about ambient temperature to about 500° C. are preferred. Preferably, the method is performed at about 200° C.

In preferred embodiments, the catalyst is a metal catalyst. Preferred metals include palladium, platinum, iron, cobalt, copper, chromium, or nickel. Catalysts comprising these metals are known in the art. A preferred catalyst is Pd/C. The skilled person can determine a suitable amount of catalyst needed to perform the method.

Any Lewis acid will be suitable for the methods of the invention, however Lewis acids of the formula Ln(X)n wherein Ln is a lanthanoid; X is halide, triflate, bis(triflamide), $C_{1-6}$alkyl, aryl, amine, oxide, $C_{1-6}$alkoxide, or aryloxide; and n is 2 or 3 are preferred. A preferred Lewis acid in La(OTf)₃. Other Lewis acids include $ZnCl_2$, $ZrCl_4$, and $BiCl_3$.

Also within the scope of the invention are methods of hydrogenating the double bonds of the α,β-unsaturated ketones of the compounds of formula I of the invention to produce compounds of formula III. Such methods can be accomplished using the procedure depicted in the following scheme, wherein R₄ of the compound of formula I is hydrogen:

Scheme 1

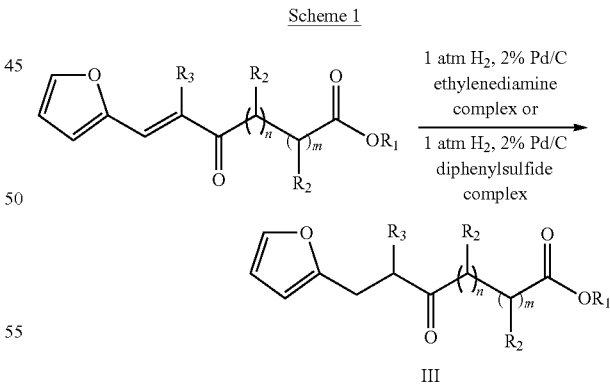

The reaction depicted in Scheme 1 can be performed in any solvents, for example, tetrahydrofuran, ethyl acetate, acetone, alkyl alcohols, for example, methanol, ethanol, propanol, isopropanol, butanol, and the like, diethyl ether, methylene chloride, water, or a combination thereof.

Compounds of formula III can be deoxidatively reduced to fuels, that is, saturated hydrocarbons, using methods known in the art or using methods described herein.

A particularly preferred compound of formula III is

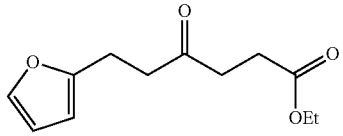 [SMILES: CCOC(=O)CCC(=O)CCc1ccco1]

The resulting compounds of formula III can be further subject to chain elongation using methods known in the art. For example, compounds of formula III can be reacted with anhydrides according to the following scheme to produce compounds of formula IV:

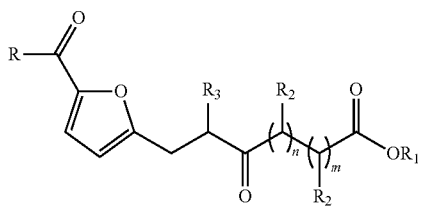

wherein $R_1$ is H or $C_{1-6}$alkyl;

each $R_2$ is independently hydrogen or $C_{1-6}$alkyl;

$R_3$ is H or $C_{1-6}$alkyl;

n is 1, 2, 3, or 4;

m is 1, 2, 3, or 4; and

R is $C_{1-6}$alkyl.

As such, methods of the invention include reacting a compound of formula III

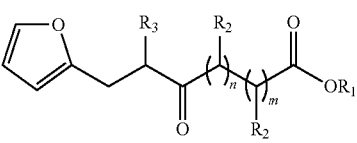

with an anhydride of the formula R—C(O)—O—C(O)—R in the presence of a Lewis acid, for a time and at a temperature sufficient to produce the compound of formula IV. Chain elongation of compounds of formula III via reaction with anhydrides can be accomplished according to the Scheme 2.

Scheme 2

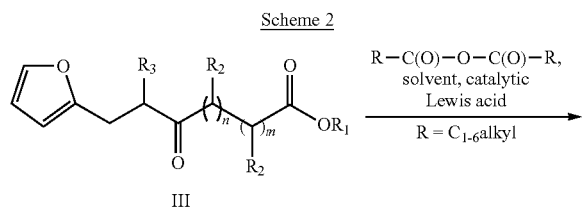

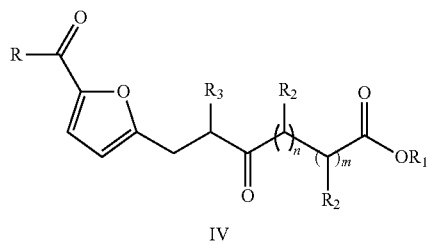

Those skilled in the art can readily identify suitable anhydrides for use in the reaction depicted in Scheme 2. Those skilled in the art can also readily identify suitable Lewis acids. Particularly preferred Lewis acids for chain elongation include, for example, $ZnCl_2$, $FeCl_3 \cdot 6H_2O$, $FeCl_3$, $ZrCl_4$, $CuCl_2$, $AlCl_3$, and Yb(triflate)$_3$. Suitable solvents can also be readily identified with preferred solvents including, for example, tetrahydrofuran, ethyl acetate, acetone, acetonitrile, diethyl ether, methylene chloride, or a combination thereof.

Compounds of formula IV can be deoxidatively reduced to fuels, that is, saturated hydrocarbons, using methods known in the art or using methods described herein.

A particularly preferred compound of formula IV is:

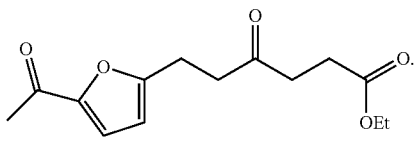 [SMILES: CCOC(=O)CCC(=O)CCc1ccc(C(C)=O)o1]

Alternatively, compounds of formula III can chain elongated by reaction with methyl vinyl ketone or acrolein according to produce compounds of formula V:

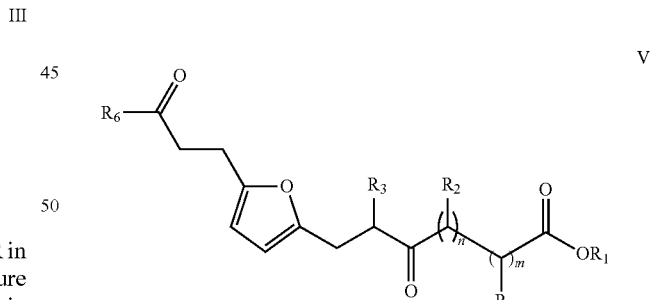

wherein $R_1$ is H or $C_{1-6}$alkyl;

each $R_2$ is independently hydrogen or $C_{1-6}$alkyl;

$R_3$ is H or $C_{1-6}$alkyl;

n is 1, 2, 3, or 4;

m is 1, 2, 3, or 4; and $R_6$ is H or $C_{1-2}$alkyl.

As such, methods of the invention include reacting a compound of formula III

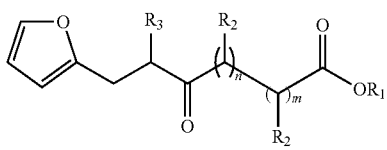

with a compound of formula

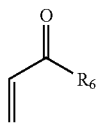

in the presence of a Lewis acid or protic acid, for a time and at a temperature sufficient to produce a compound of formula V. Preferred Lewis acids include, for example, FeCl$_3$. An exemplary method of producing compounds of formula V is depicted in Scheme 3.

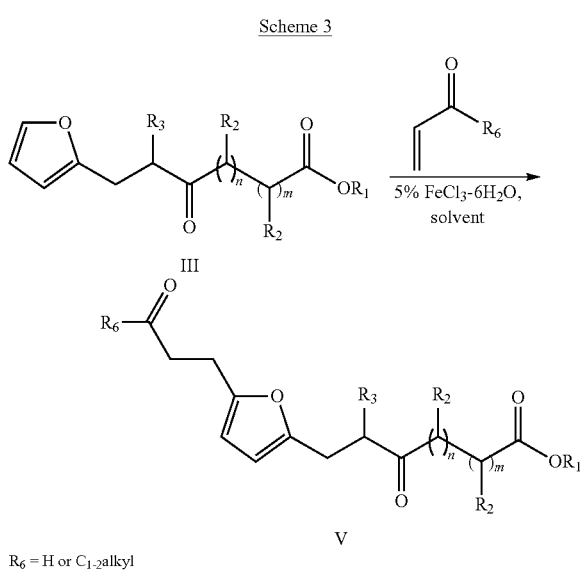

$R_6$ = H or C$_{1-2}$alkyl

Other preferred reactants include Lewis acids and protic acids, for example, p-toluenesulfonic acid, NaHSO$_3$, AlCl$_3$, and ZrCl$_4$. Suitable solvents can also be readily identified with preferred solvents including, for example, tetrahydrofuran, acetonitrile, ethyl acetate, acetone, diethyl ether, methylene chloride, or a combination thereof.

Compounds of formula V can be deoxidatively reduced to fuels, that is, saturated hydrocarbons, using methods known in the art or using methods described herein.

Particularly preferred compounds of formula V are

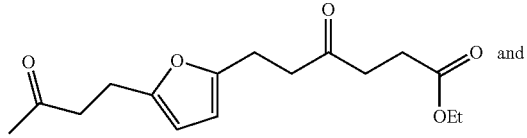

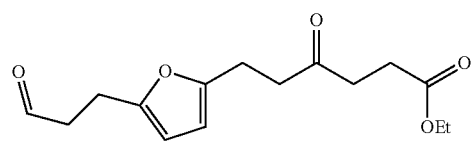

Also within the scope of the invention are methods of chain elongating compounds of formula III to produce compounds of formula IV:

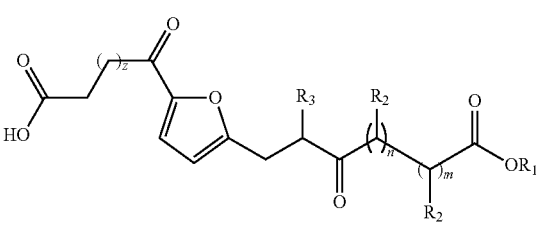

wherein
R$_1$ is H or C$_{1-6}$alkyl;
each R$_2$ is independently hydrogen or C$_{1-6}$alkyl;
R$_3$ is H or C$_{1-6}$alkyl;
n is 1, 2, 3, or 4;
m is 1, 2, 3, or 4; and
z is 1 to 7.

These methods include reacting a compound of formula III

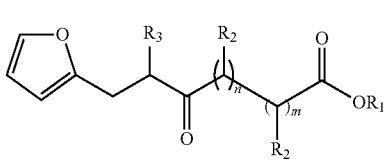

with maleic anhydride, an anhydride of the formula

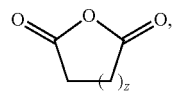

maleic acid, fumaric acid, muconic acid, 2,5-furan dicarboxylic acid, or a dicarboxylic acid of the formula

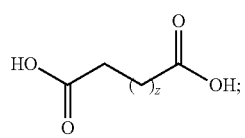

in the presence of a Lewis acid or dehydrating agent; for a time and at a temperature sufficient to produce the compound of formula VI.

In preferred embodiments, the anhydride of the formula

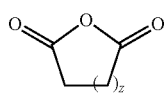

is succinic anhydride, glutaric anhydride, adipic anhydride, pimelic ahydride, suberic anhydride, azelaic anhydride, or sebacic anhydride.

In other preferred embodiments, the dicarboxylic acid of the formula

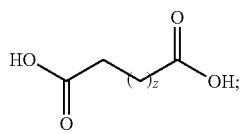

is succinic acid, glutaric acid, adipic acid, pimelic acid, suberic acid, azelaic acid, or sebacic acid.

Chain elongation of compounds of formula III can be accomplished by reaction with cyclic anhydrides according to Scheme 4 to produce compounds of formula VI Scheme 4

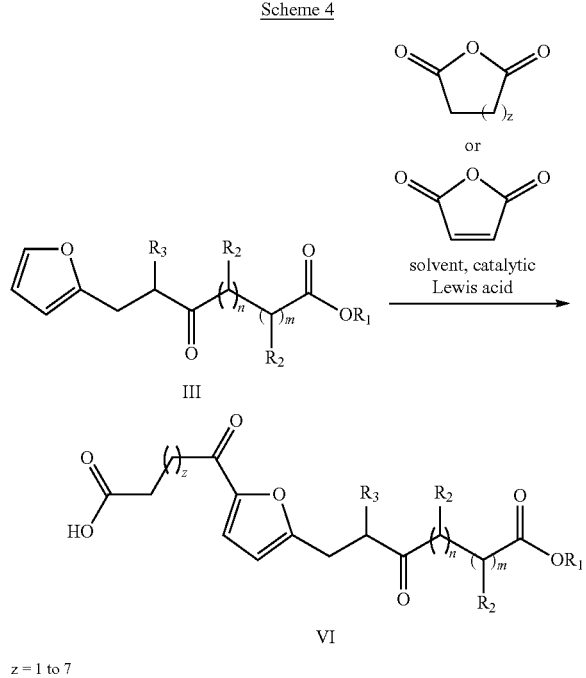

z = 1 to 7

Preferred cyclic anhydrides include, for example, maleic anhydride, succinic anhydride, glutaric anhydride, adipic anhydride, pimelic ahydride, suberic anhydride, azelaic anhydride, and sebacic anhydride.

Chain elongation of compounds of formula III can also be accomplished by reaction with dicarboxylic acids according to Scheme 5 to produce compounds of formula VI.

Scheme 5

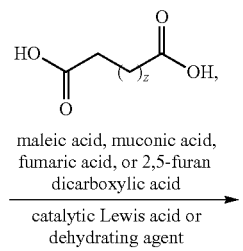

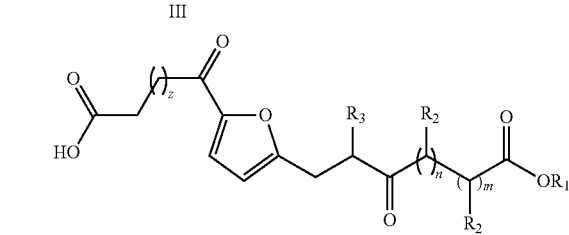

z = 1 to 7

Preferred dicarboxylic acids include succinic acid, glutaric acid, adipic acid, pimelic acid, suberic acid, azelaic acid, sebacic acid, maleic acid, fumaric acid, muconic acid, and 2,5-furan dicarboxylic acid. Preferred Lewis acids include, for example, $AlCl_3$ and the lanthanide triflates. Preferred dehydrating agents include protic acids, for example, sulfuric acid. Another preferred dehydrating agent is $P_2O_5$.

With certain dicarboxylic acids, it may be necessary to activate the dicarboxylic acid for reaction with a compound of formula III. Such activation is known to those skilled in the art and can include activation such as that shown in Scheme 6:

Scheme 6

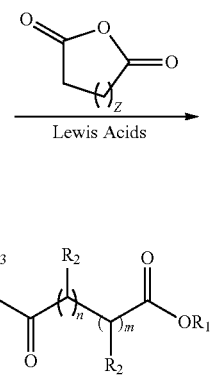

Z = 1 to 7 carbons: all symmetric anhydrides. Sucinnic, glutaric, adipic, pimelic, suberic, azelaic, sebasic anhydrides.

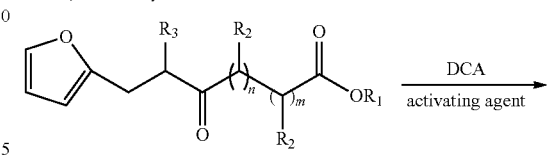

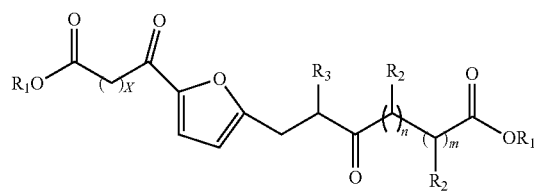

DCA = dicarboxylic acid.
Examples of DCAs = maleic, muconic, 2,5-furan dicarboxylic acid, fumaric.

Within the scope of Scheme 6, examples of dicarboxylic acids ("DCAs") include maleic, muconic, 2,5-furan dicarboxylic acid, fumaric acid, and the like. Activating agents include, for example, Lewis acids and dehydrating acids. Muconic furan dicarboxylic acid and fumaric acid will not form symmetrical anhydrides. These can be activated for the Friedel-Crafts reaction by converting the diacids to the mono ester acid chloride and used in the reaction scheme shown in Scheme 6.

Compounds of formula VI can be deoxidatively reduced to fuels, that is, saturated hydrocarbons, using methods known in the art or using methods described herein.

Scheme 7 depicts alternative methods of making compounds within the scope of the invention. Within the scope of Scheme 7, examples of dicarboxylic acids ("DCAs") include maleic, muconic, 2,5-furan dicarboxylic acid, fumaric acid, and the like. Activating agents include Lewis acids and dehydrating acids, as described herein. Muconic dicarboxylic acid and fumaric acid will not form symmetrical anhydrides. These can be activated for the Friedel-Crafts reaction by converting the diacids to the mono ester acid chloride and used in the reaction scheme shown in Scheme 7.

Scheme 7

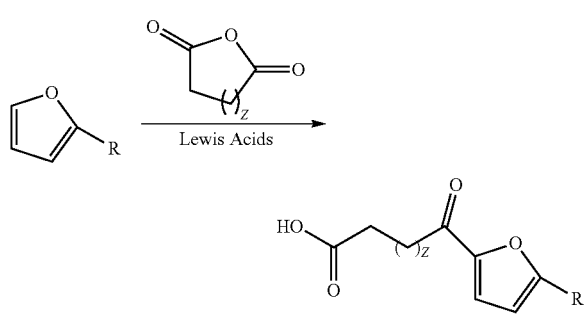

R = H, C1-C10, COOH, CHO, CH2OH
Z = 1 to 7 carbons: all symmetric anhydrides. Sucinnic, glutaric, adipic, pimelic, suberic, azelaic, sebasic anhydrides.

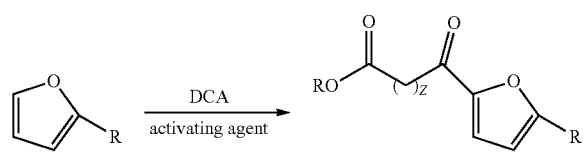

Z = 1 to 7 carbons:
DCA = dicarboxylic acid.
Examples of DCAs = maleic, muconic, 2,5-furan dicarboxylic acid, fumaric.

Compounds within the scope of the invention can be reductively deoxygenated according to, for example, Scheme 8.

Scheme 8

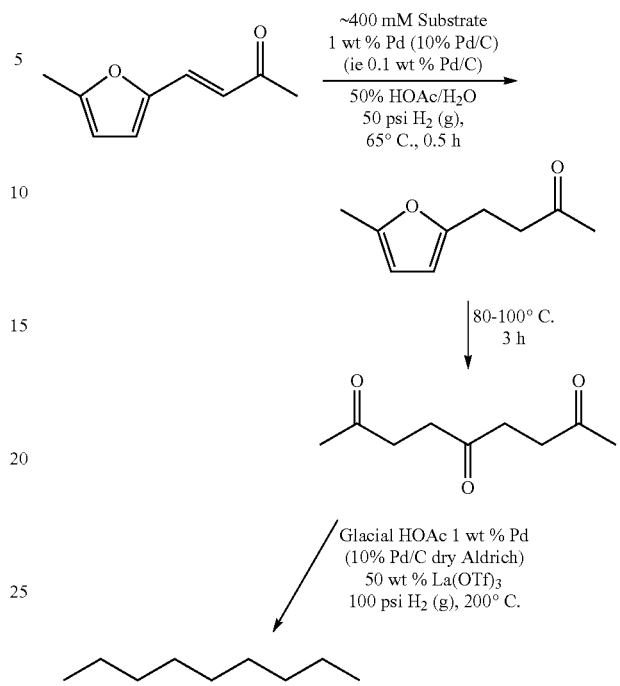

As used herein, "alkyl" refers to a branched or straight chain saturated aliphatic hydrocarbon radical of from 1 to 20 carbons, i.e., $C_{1-20}$alkyl. The term alkyl includes, but is not limited to, radicals such as methyl, ethyl propyl, butyl, pentyl, hexyl, heptyl, octyl, nonyl, decyl, undecyl, docecyl, and the like. Branked alkyl radicals include, for example, isobutyl, tert-butyl, isopropyl, and the like.

As used herein, "substituted alkyl" refers to and alkyl radical wherein one, two or three hydrogens has been replaced with a functional group. Preferred functional groups include —OH, halogen (F, Cl, Br), oxo (═O), alkoxy (alkyl-O—), —COOH, and the like.

As used herein, "deoxidative reduction" refers to a process wherein reductive conditions are employed that not only reduce the compound of interest, but also deoxygenate the compound of interest.

As used herein, "hydrocarbon" refers to an organic compound wherein the majority of the atoms in the compound are carbon and hydrogen. In an "oxygenated hydrocarbon," within the scope of the invention, the majority of the atoms in the compound are carbon and hydrogen, with a minority of the atoms of the compound being oxygen.

As used herein, "saturated hydrocarbon" refers to organic compounds wherein the majority of the atoms in the compound are carbon and hydrogen and all bonds within the compound are single bonds.

As used herein, "unsaturated hydrocarbon" refers to organic compounds wherein the majority of the atoms in the compound are carbon and hydrogen and wherein at least one bond within the compound is a double bond.

Hydrogenation reactions described herein were carried out in a 50 mL Autoclave Engineers, high-pressure reactor connected to the custom-build hydrogen supply and uptake measurement system, allowing for real-time measurement of hydrogen uptake at constant pressure (dynamic mode) or the determination of the total amount of hydrogen consumed after completion of the reaction (totalizer mode) using a thermal mass flow meter.

In dynamic mode the reactor is charged with substrate, solvent (where applicable) and catalyst encapsulated in a sealed glass ampoule. The reactor is then sealed, pressurized to the desired level with an open connection and heated to the set temperature. The reaction is then started by switching on the stirrer in the reactor, shattering the glass ampoule and releasing the catalyst (time=0) with immediate measurement of the hydrogen uptake rate. Since the relative volume of the reservoirs (7570 mL=2 US gallons) is 300 times that of the head space of the reactor (25 mL) and total substrates amounts can be adjusted as desired limiting total hydrogen consumption. The reaction order of hydrogen itself (by definition=0 in any given run in this method) can then be determined by carrying out experiments at different hydrogen pressures all other parameters being equal.

In totalizer mode, the reactor is charged with substrate, solvent (where applicable) and catalyst, pressurized from the reservoirs to the desired level and then isolated from the hydrogen feed system. The reaction is then started by switching on the heater and stirrer. In this case the pressure in the reactor will drop as hydrogen is consumed. Completion of the reaction is indicated by reaching a constant pressure as indicated by the pressure gauge. Upon completion the reactor is allowed to cool to ambient temperature and then re-pressurized to the starting pressure For both methods the actual moles of hydrogen gas consumed were determined by applying the virial gas theorem, i.e., an expanded ideal gas law as $$Z = \frac{PV_m}{RT} = 1 + \frac{B}{V_m} + \frac{C}{V_m^2} + \ldots$$

where B=14.38 cm$^3$/mol and C=370 cm$^3$/mol (at standard conditions—see lines 7 & 8 of Chart 2; Lit.: Michels, A. D. G., W.; Ten Seldam, C. A. *Physica* 1960, 393.) are the second and third virial coefficients, $V_m$ is the molar volume, and Z is the compression factor. Note that in both methods the actual measurement of the gas flow is carried out at the ambient temperature of the mass flow meter, which is calibrated for a temperature of 293.15 K and a pressure of 1013.25 bar or 14.69595025 psi regardless of the reaction temperature and pressure.

EXAMPLES

Example 1

Preparation of (E)-ethyl 7-(5-(hydroxymethyl)furan-2-yl)-5-oxohept-6-enoate

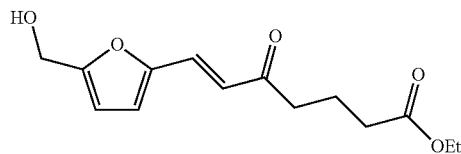 [SMILES: CCOC(=O)CCCC(=O)/C=C/c1ccc(CO)o1]

In a 250 mL ground glass single necked, 24/40, round bottom flask was placed 30 g of hydroxymethyl furfural (HMF) (238 mmol), 38.4 g of homoethyllevulinate (243 mmol) and 35 mL of ethanol. Stirring was started and the system was purged with argon. To this mixture, at ambient temperature, was added 2 mL of pyrrolidine (23.9 mmol). During the addition, the mixture darkened. Once the mixture was mixed well, it was then chilled using an ice bath. Once the mixture had obtained a temperature of 5° C. or less, 7.14 mL of acetic acid was added dropwise (mixture was still over an atmosphere of argon). Once completed, the ice bath was removed and the mixture stirred overnight. The reaction was monitored for completion by $^1$H and $^{13}$C NMR spectroscopy (as determined by disappearance of the aldehyde proton or carbon resonance). Once determined to be complete (12 h for this reaction) the mixture was placed on a rotovap and the ethanol and water were mostly removed. The mixture was then chilled and cold water was added. A yellow solid precipitated out and it was washed with cold water. The solids were dried under a vacuum to give 58.92 g of the product (93%). The water washings were extracted with ethyl acetate and about 3 more grams of product was recovered. $\delta_H$ (CDCl$_3$) 1.25 (t, J=7 Hz, 3H), 2.0 (app p, J=7 Hz, 2H), 2.37 (t, J=7 Hz, 2H), 2.67 (t, J=7 Hz, 2H), 4.13 (q, J=7 Hz, 2H), 4.65 (s, 2H), 6.39 (m, 1H), 6.62 (m, 2H), 7.28 (m, 1H). $\delta^{13}_C$ (CDCl$_3$) 199.4, 173.5, 157.1, 150.96, 128.9, 123.1, 117.0, 110.6, 60.6, 57.7, 40.4, 33.6, 19.6, 14.4.

Example 2

Preparation of (E)-ethyl 7-(5-methylfuran-2-yl)-5-oxohept-6-enoate

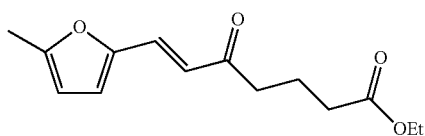 [SMILES: CCOC(=O)CCCC(=O)/C=C/c1ccc(C)o1]

In a 250 mL ground glass single necked, 24/40, round bottom flask was placed 40 g of methyl furfural (396 mmol), 62.6 g of homoethyllevulinate (396 mmol). Stirring was started and the system was purged with argon. To this mixture, at ambient temperature, was added 3.3 mL of pyrrolidine (39.5 mmol). During the addition, the mixture darkened. Once the mixture was mixed well, it was then chilled using an ice bath. Once the mixture had obtained a temperature of 5° C. or less, 6.0 mL of acetic acid was added dropwise (mixture was still over an atmosphere of argon). Once completed, the ice bath was removed and the mixture stirred overnight. The reaction was monitored for completion by $^1$H and $^{13}$C NMR spectroscopy (as determined by disappearance of the aldehyde proton or carbon resonance). Once determined to be complete (12 h for this reaction) the mixture was placed on a rotovap and the ethanol and water were mostly removed. Purification by silica gel chromatography gave 90.66 g (95%). $\delta_H$(CDCl$_3$) 1.25 (t, J=7 Hz, 3H), 1.98, (app p, J=7 Hz, 2H), 2.40 (s, 3H), 2.37 (t, J=7 Hz, 2H), 2.65 (t, J=7 Hz, 2H), 4.17 (q, J=7 Hz, 2H), 6.09 (s, 1H), 6.56 (m, 2H), 7.25 (m, 1H). $\delta^{13}{}_C$(CDCl$_3$) 198.7, 172.9, 155.4, 149.2, 128.4, 121.1, 117.3, 108.8, 59.9, 39.7, 33.0, 19.1, 13.8, 13.5.

Example 3

Preparation of (E)-ethyl 6-(5-(hydroxymethyl)furan-2-yl)-4-oxohex-5-enoate

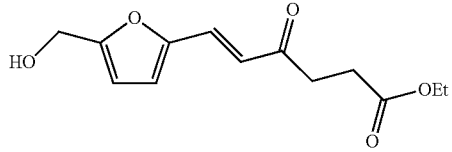 [SMILES: CCOC(=O)CCC(=O)/C=C/c1ccc(CO)o1]

11.3 mL of ethyl levulinate (79.2 mmol) was placed in a ground glass single necked, 24/40, round bottom flask and stirring was begun. This was then chilled with an ice bath. In air, the pyrrolidine (1.25 mL, 15.8 mmol) and acetic acid (0.91 mL, 15.8 mmol) was then added. Hydroxymethyl furfural (HMF) (10.01 g, 79.2 mmol) was then added and solution darkened. The cooling bath was then removed and the solution was stirred at ambient temperature until the reaction was complete (by $^1$H and $^{13}$C NMR). The reaction was then purified by silica gel chromatography (using an ethyl acetate/hexane gradient). 17.1 g of product was obtained (85%). $\delta_H$(CDCl$_3$) 1.21 (t, J=7 Hz, 3H), 2.60 (t, J=6.6 Hz, 2H), 2.86 (t, J=6.6 Hz, 2H), 4.09 (q, J=7 Hz, 2H), 4.56 (s, 2H), 6.19 (m, 1H), 6.56 (m, 2H), 7.25 (m, 1H). $\delta^{13}{}_C$(CDCl$_3$) 197.6, 172.6, 157.1, 150.0, 128.6, 120.0, 116.7, 109.8, 60.3, 56.8, 35.1, 27.8, 13.6.

Example 4

Preparation of (E)-ethyl 6-(furan-2-yl)-4-oxohex-5-enoate

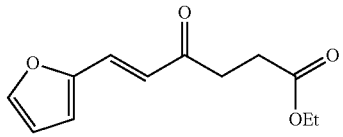 [SMILES: CCOC(=O)CCC(=O)/C=C/c1ccco1]

The same process was used as described for (E)-ethyl 6-(5-(hydroxymethyl)furan-2-yl)-4-oxohex-5-enoate. (E)-ethyl 6-(furan-2-yl)-4-oxohex-5-enoate can be distilled. Distillation yielded 17.93 g (78%). $\delta_H$(CDCl$_3$) 1.25 (t, J=7 Hz, 3H), 2.66 (t, J=6.6 Hz, 2H), 2.94 (t, J=6.6 Hz, 2H), 4.12 (q, J=7 Hz, 2H), 6.48 (m, 1H), 6.65 (m, 2H), 7.34 (d, J=16 Hz, 1H), 7.49 (d, J=1.5 Hz, 1H). $\delta^{13}{}_C$ (CDCl$_3$) 197.2, 172.4, 150.5, 144.6, 128.5, 122.5, 115.4, 112.1, 60.15, 35.2, 27.8, 13.7.

Example 5

Preparation of 1-(5-Hydroxymethyl-furan-2-yl)-undec-1-en-3-one

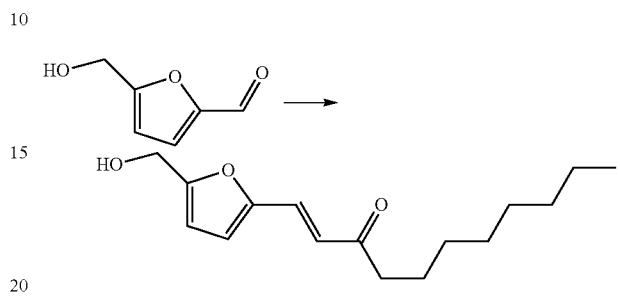

In a 50 mL ground glass, single necked, 14/20, round bottom flask was placed 0.138 mL of pyrrolidine (1.65 mmol) and 2 mL of ether. To this was added 0.094 mL of acetic acid. The mixture was chilled using an ice bath. To this, 0.234 g of decane-2-one (1.5 mmol) was added as an ether solution (2 mL) dropwise. The mixture was stirred for 30 min and 0.189 g of hydroxymethyl furfural (HMF) was added (1.5 mmol). The mixture was then warmed to ambient temperature and stirred for 48 h. Purification using silica gel chromatography yielded 0.2773 g of the product (70% yield). The proton and $^{13}$C NMR spectra were consistent with the assigned structure.

This reaction was also performed by replacing the ether with THF and EtOH to yield similar results.

Example 6

Preparation of 1-Furan-2-yl-undec-1-en-3-one

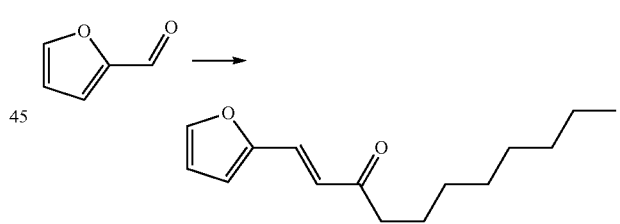

1-Furan-2-yl-undec-1-en-3-one was prepared using a procedure similar to that described for the synthesis of 1-(5-Hydroxymethyl-furan-2-yl)-undec-1-en-3-one using either ethanol as solvent or using no solvent.

Example 7

General Procedure for the Conversion of Oxygenated, Unsaturated Hydrocarbons to Saturated Hydrocarbons The oxygenated, unsaturated hydrocarbon is treated with hydrogen under pressures of about atmospheric pressure to about 500 psi, in the presence of a catalyst, preferably Pd/C, and a Lewis acid, preferably La(OTf)$_3$, at a temperature of from ambient temperature to about 500° C. The reaction is carried out under acidic conditions, i.e., pH of less than 7, preferably in the presence of acetic acid. The reaction is complete in from about 5 minutes to about 48 hours.

Example 8

Preparation of n-Nonane

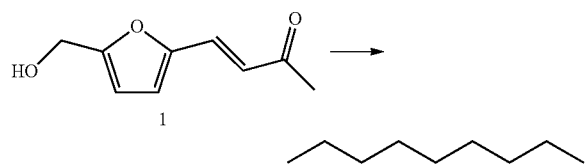

Compound 1 (0.25 g) was combined in acetic acid (1 mL) with Pd/C (10% by wt Pd, 0.125 g), La(OTf)$_3$ (0.100 g) and placed in a sealed vessel under H$_2$ pressure (100 psi). The vessel was heated to 200° C. for 15 hours. The heating source was removed and the vessel allowed to cool to room temperature. The pressure was released and reaction mixture extracted from the vessel with methylene chloride (2×2 mL) and water (2×2 mL). The combined layers were filtered and the organic layer separated, dried over NaSO$_4$ and solvent removed in vacuo yield n-nonane as a colorless oil (67% isolated yield) as confirmed by GC-MS. $^1$H NMR (400 MHz, CDCl$_3$) δ 1.29 (m, 14H), 0.88 (s, 6H). $^{13}$C NMR (101 MHz, CDCl$_3$) δ 32.14, 29.73, 29.57, 22.81, 14.23.

Example 9

Preparation of n-Dodecane

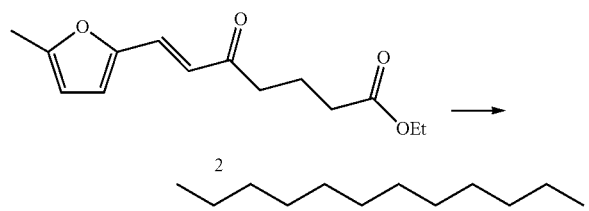

Compound 2 (0.25 g) was combined in acetic acid (1 mL) with Pd/C (10% by wt Pd, 0.125 g), La(OTf)$_3$ (0.100 g) and placed in a sealed vessel under H$_2$ pressure (100 psi). The vessel was heated to 200° C. for 15 hours. At this time the heating source was removed and the vessel allowed to cool to room temperature. The pressure was released and reaction mixture extracted from the vessel with methylene chloride (2×2 mL) and water (2×2 mL). The combined layers were filtered and the organic layer separated, dried over NaSO$_4$ and solvent removed in vacuo to yield n-dodecane as a colorless oil (76% isolated yield) as confirmed by GC-MS. $^1$H NMR (400 MHz, CDCl$_3$) δ 1.27 (m, 20H), 0.88 (m, 6H). $^{13}$C NMR (101 MHz, CDCl$_3$) δ 32.11, 29.85, 29.58, 22.86, 14.19.

Example 10

Stepwise Preparation of n-Dodecane

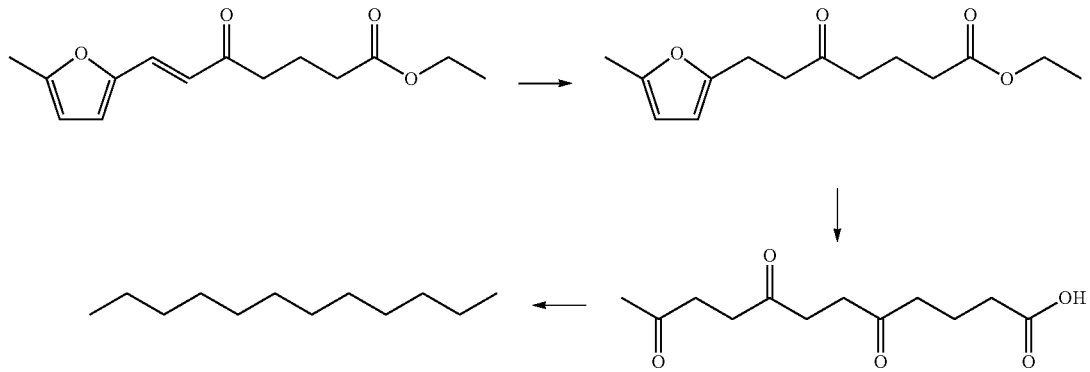

Unsaturated C$_{12}$ (250 mg, 1.00 mmol) was dissolved in methanol (15 mL) and added to a round bottom flask containing wetted Pd/C (125 mg of 10 wt % Pd/C, 0.120 mmol Pd, 12 mol % Pd relative to substrate). The mixture was put under 1 atmosphere of H$_2$ and heated at 60° C. for 1 hour to yield a pale yellow solution of saturated C12 as confirmed by NMR ($^1$H NMR (400 MHz, CDCl$_3$) δ 5.74 (d, 1H), 4.03 (q, J=7.1, 2H), 2.76 (t, J=7.3, 1H), 2.70-2.54 (m, 2H), 2.50-2.33 (m, 2H), 2.31-2.18 (m, 2H), 2.14 (s, 2H), 2.11-1.99 (m, 1H), 1.88-1.71 (m, 2H), 1.16 (t, J=7.1, 3H). $^{13}$C NMR (101 MHz, CDCl$_3$) δ 208.65, 173.00, 152.49, 150.33, 105.80, 105.66, 60.18, 41.42, 40.82, 33.11, 22.11, 18.72, 14.08, 13.30).

HCl (1 mL) was added to the solution and the flask was then equipped with a condenser, opened to the air and heated at 100° C. for 3 hours to yield a colorless solution. The solvent was removed and resultant solid extracted with dichloromethane (3×5 mL), dried over MgSO$_4$, filtered and solvent removed in vacuo to yield the triketone acid (223 mg, 91% yield) ($^1$H NMR (400 MHz, CDCl$_3$) δ 2.71 (m, 8H), 2.54 (m, 3H), 2.35 (m, 3H), 1.88 (m, 3H). $^{13}$C NMR (101 MHz, CDCl$_3$) δ 208.54, 207.91, 206.90, 173.56, 36.99, 36.11, 36.07, 36.03, 32.88, 30.89, 29.82, 18.57).

The triketone acid (245 mg, 0.91 mmol) was dissolved in 1M HCl (5 mL) and added along with Pd/C (245 mg of 10 wt % Pd/C, 0.230 mmol Pd, 23 mol % Pd relative to substrate) to a stainless steel Swagelok equipped sample tube. The tube was then pressurized with 300 psi H$_2$ and heated to 200° C. for 14 hours. Upon cooling, the pressure was released and reaction mixture extracted from the vessel with methylene chloride (2×2 mL) and water (2×2 mL). The combined layers were filtered and the organic layer separated, dried over NaSO$_4$ and solvent removed in vacuo to yield dodecane as a colorless oil (118 mg, 76%) as confirmed by GC-MS. $^1$H NMR (400 MHz, CDCl$_3$) δ 1.27 (m, 20H), 0.88 (m, 6H). $^{13}$C NMR (101 MHz, CDCl$_3$) δ 32.11, 29.85, 29.58, 22.86, 14.19.

Example 11

Preparation of n-Pentadecane

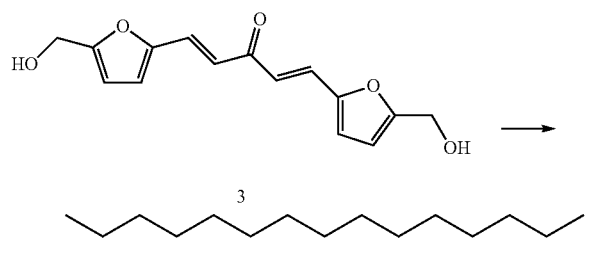

Compound 3 (0.25 g) was combined in acetic acid (1 mL) with Pd/C (10% by wt Pd, 0.250 g), La(OTf)$_3$ (0.200 g) and placed in a sealed vessel under H$_2$ pressure (100 psi). The vessel was heated to 200° C. for 15 hours. At this time the heating source was removed and the vessel allowed to cool to room temperature. The suspension was removed from the vessel and diluted with dichloromethane and 2-propanol and filtered to remove the catalyst. The solvent was removed under vacuum and redissolved in benzene-d6. The pressure was released and reaction mixture extracted from the vessel with methylene chloride (2×2 mL) and water (2×2 mL). The combined layers were filtered and the organic layer separated, dried over NaSO$_4$ and solvent removed in vacuo to yield pentadecane as a colorless oil (65% isolated yield) as confirmed by GC-MS. $^1$H NMR (400 MHz, CDCl$_3$) δ 1.27 (m, 26H), 0.88 (m, 6H). $^{13}$C NMR (101 MHz, CDCl$_3$) δ 32.09, 29.87, 29.53, 22.82, 14.15.

Example 12

Stepwise Preparation of n-Pentadecane

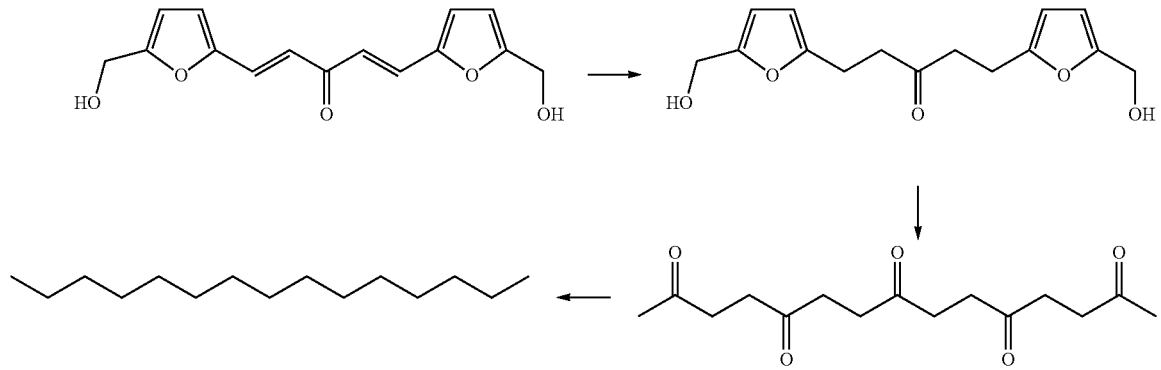

Unsaturated C$_{15}$ precursor (250 mg, 1.00 mmol) was dissolved in glacial acetic acid (15 mL) and added to a round bottom flask containing Pd/C (125 mg of 10 wt % Pd/C, 0.120 mmol Pd, 12 mol % Pd relative to substrate). The mixture was put under 1 atmosphere of H$_2$ and heated at 100° C. for 12 hours to yield a pale yellow solution of pentaketone as confirmed by NMR ($^1$H NMR (400 MHz, CDCl$_3$) δ 2.73 (m, 16H), 2.18 (s, 6H). $^{13}$C NMR (101 MHz, CDCl$_3$) δ 207.93, 207.88, 207.18, 36.97, 36.11, 36.06, 36.02, 29.85).

The solution was transferred to a stainless steel pressure reactor with La(OTf)$_3$ (170 mg, 0.290 mmol) pressurized with 300 psi H$_2$ and heated to 200° C. for 14 hours. Upon cooling, the pressure was released and reaction mixture extracted from the vessel with methylene chloride (2×2 mL) and water (2×2 mL). The combined layers were filtered and the organic layer separated, dried over NaSO$_4$ and solvent removed in vacuo to yield pentadecane as a colorless oil (97 mg, 65%) as confirmed by GC-MS. $^1$H NMR (400 MHz, CDCl$_3$) δ 1.27 (m, 26H), 0.88 (m, 6H). $^{13}$C NMR (101 MHz, CDCl$_3$) δ 32.09, 29.87, 29.53, 22.82, 14.15.

Example 13

Preparation of Ethyl 6-(furan-2-yl)-4-oxohexanoate

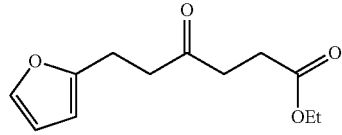 [SMILES: CCOC(=O)CCC(=O)CCc1ccco1]

In a round bottom flask was placed 1.334 g (6.000 mmol) of (E)-ethyl 6-(furan-2-yl)-4-oxohex-5-enoate. 6 mL of acetonitrile was added and stirring was begun. To this was added 0.064 g Pd/C (en) and hydrogen was added using a balloon (~1 atm). The reaction mixture was stirred for 48 h and the mixture was then purified by flash column chromatography using 15% ether/hexane, v/v. Purification gave rise to 0.4817 g (73%) of the saturated system $^1$H (CDCl$_3$) δ 1.25 (t, J=7 Hz, 3H), 2.6 (m, 2H), 2.8 (m, 2H), 2.9 (m, 2H), 3.0 (m, 2H), 4.16 (q, J=7 Hz), 6.0 (1H), 6.3 (1H), 7.3 (1H).

Example 14

Preparation of Ethyl 6-(5-acetylfuran-2-yl)-4-oxohexanoate

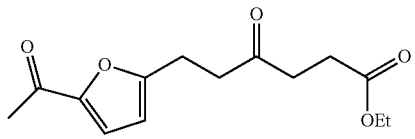 [SMILES: CCOC(=O)CCC(=O)CCc1ccc(C(C)=O)o1]

In a round bottom flask was placed 0.224 g (1.00 mmol) of ethyl 6-(furan-2-yl)-4-oxohexanoate. 1 mL of acetonitrile was added and stirring was begun. To this was added 0.031 g (0.050 mmol) of ytterbium trifluoromethanesulfonate [Yb (OTf)$_3$] and 0.204 g (2.00 mmol) of acetic anhydride was added. The reaction mixture was stirred overnight and the mixture was then purified by flash column chromatography using 30% ether/hexane, v/v. Purification gave rise to 0.1440 g (54%) of the acylated furan. δ $^1$H (CDCl$_3$) 1.32 (t, J=7 Hz, 3H), 2.45 (s, 3H), 2.65 (m, 2H), 2.8 (t, J=5 Hz, 2H), 2.9 (m, 2H), 3.0 (m, 2H), 4.16 (q, J=7 Hz), 6.22 (d, J=3.5 Hz, 1H), 7.12 (d, J=3.5 Hz, 1H).

Example 15

Preparation of Ethyl 4-oxo-6-(5-(3-oxobutyl)furan-2-yl)hexanoate

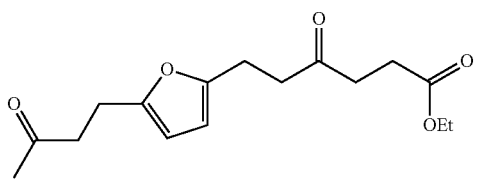 [SMILES: CCOC(=O)CCC(=O)CCc1ccc(CCC(C)=O)o1]

In a round bottom flask was placed 0.366 g (1.63 mmol) of ethyl 6-(furan-2-yl)-4-oxohexanoate. 1.6 mL of acetonitrile was added and stirring was begun. To this was added 0.031 g (0.163 mmol) of p-toluenesulfonic acid mono hydrate and 0.172 g (2.5 mmol) of methyl vinyl ketone was added. The reaction mixture was stirred for 1 h and the mixture was then purified by flash column chromatography using 25% ether/hexane, v/v. Purification gave rise to 0.2432 g (51%) of the alkylated furan. δ $^1$H (CDCl$_3$) 1.25 (t, J=7 Hz, 3H), 2.16 (s, 3H), 2.6 (m, 2H), 2.73-2.88 (m, 10H), 4.13 (q, J=7 Hz, 2H), 5.86 (s, 2H): δ $^{13}$C (CDCl$_3$) 14.4, 22.40, 22.49, 28.2, 30.2, 37.3 41.1, 42.0, 60.9, 106.0, 153.2, 153.24, 173.0, 207.6, 207.7

Example 16

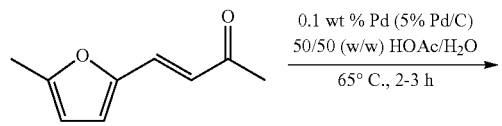

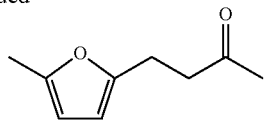

To a 50 mL round bottom flask, 0.5625 g (3.75 mmol) of unsaturated C$_9$ precursorwas dissolved in a H$_2$O/HOAc mixture (50% by wt) acetic acid in H$_2$O (15 mL) and Pd/C added (13 mg of 5 wt % Pd/C, 0.006 mmol Pd, 0.16 mol % Pd relative to substrate). The solution was added to a round bottom flask, put under an atmosphere of H$_2$ using a balloon and heated at 65° C. for 2-3 hours to yield a near colorless solution of the hydrogenated product.

Example 17

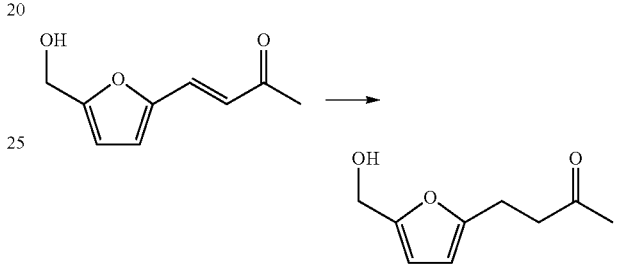

Unsaturated C$_9$ precursor (166 mg, 1.00 mmol) was dissolved in MeOH (1 mL) and added dropwise to a stirred mixture of Mg turnings (49 mg, 2.0 mmol) in MeOH (5 mL). On addition of A, gas evolution was observed and a precipitate formed. Stirring was allowed to continue for 10 hours. The solution was filtered and solvent removed in vacuo to yield 98 mg of the saturated C9 as a yellow powder (56% yield).

Unsaturated C$_9$ precursor (166 mg, 1.00 mmol) was dissolved in a 50% v/v solution of acetic acid in H$_2$O (5 mL) containing ammonium formate (126 mg, 2.00 mmol) and Pd/C (83 mg of 10 wt % Pd/C, 0.080 mmol Pd, 8 mol % Pd relative to substrate). The mixture was heated at 100° C. for 10 hours, cooled to room temperature and filtered. The aqueous layer was extracted with dichloromethane (3×5 mL), dried over MgSO$_4$, filtered and solvent removed in vacuo to yield the saturated C9 (142 mg, 85% yield).

Unsaturated C$_9$ precursor (166 mg, 1.00 mmol) was dissolved in a 50% v/v solution of acetic acid in H$_2$O (5 mL) and 5 wt % Pd/C (83 mg of 10 wt % Pd/C, 0.080 mmol Pd, 8 mol % Pd relative to substrate). The resulting mixture was added to a stainless steel sample tube, pressurized with H$_2$ gas (100 psi) and heated at 60° C. for 10 hours, cooled to room temperature, the pressure released and the resultant mixture filtered. The aqueous layer was extracted with dichloromethane (3×5 mL), dried over MgSO$_4$, filtered and solvent removed in vacuo to yield the saturated C9 (155 mg, 92% yield).

Unsaturated C$_9$ precursor (166 mg, 1.00 mmol) was dissolved in methanol (5 mL) and added to wetted Pd/C (83 mg of 10 wt % Pd/C, 0.080 mmol Pd, 8 mol % Pd relative to substrate). The mixture was placed in a round bottom flask and put under 1 atmosphere of H$_2$ gas and heated at 60° C. for 1 hour, cooled to room temperature and taken to dryness. The solid was extracted with dichloromethane (3×5 mL), dried over MgSO$_4$, filtered and solvent removed in vacuo to yield the saturated C9 in quantitative yield. $^1$H NMR (400 MHz, CDCl$_3$) δ 6.00 (m, 2H), 4.48 (s, 2H), 3.22 (m, 2H), 3.10-2.32 (m, 4H), 2.12 (s, 3H). $^{13}$C NMR (101 MHz, CDCl$_3$) δ 207.85, 154.49, 152.80, 108.44, 105.96, 57.18, 41.58, 29.87, 22.18.

Example 18

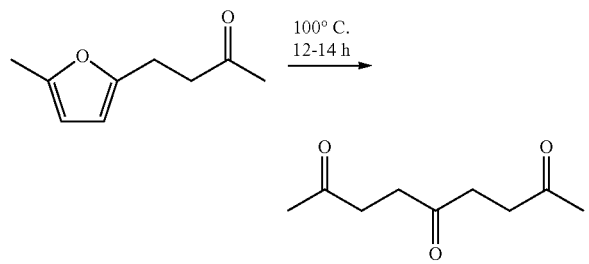

The saturated C$_9$ species was dissolved in a H$_2$O/HOAc mixture (50% by wt) acetic acid in H$_2$O (15 mL) and a reflux condenser was attached to the round bottom flask. The reaction solution was heated to 100° C. overnight (~12-14 h) to yield a dark orange/red solution to yield the triketone in 98% isolated yield. $^1$H NMR (400 MHz, CDCl$_3$) δ 2.92-2.44 (m, 8H), 2.42-1.97 (m, 6H). $^{13}$C NMR (101 MHz, CDCl$_3$) δ 207.99, 207.30, 36.99, 36.09, 29.87.

Example 19

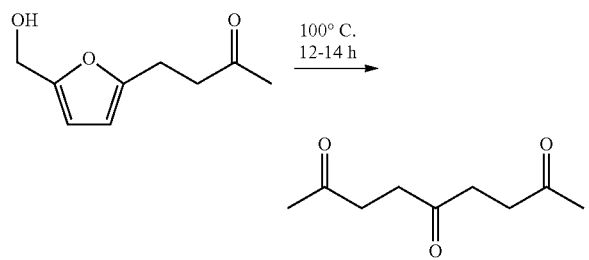

Saturated C$_9$ precursor (0.168 g, 1.00 mmol) was dissolved in 50% v/v solution of acetic acid (5 mL) in H$_2$O and placed in a round bottom flask with a condenser and heated at 100° C. for 3 hours to provide a colorless solution, that when cooled could be neutralized with NaHCO$_3$ and extracted with dichloromethane (3×5 mL), dried over MgSO$_4$, filtered and solvent removed in vacuo to yield non-2,5,7-trione (166 mg, 98% yield).

Saturated C$_9$ precursor (0.168 g, 1.00 mmol) was dissolved in a 1M solution of HCl in methanol (10 mL) and placed in a round bottom flask with a condenser and heated at 100° C. for 3 hours to provide a colorless solution. The solvent was removed and extracted with dichloromethane (3×5 mL), dried over MgSO$_4$, filtered and solvent removed in vacuo to yield non-2,5,7-trione in near quantitative yield. $^1$H NMR (400 MHz, CDCl$_3$) δ 2.92-2.44 (m, 8H), 2.42-1.97 (m, 6H). $^{13}$C NMR (101 MHz, CDCl$_3$) δ 207.99, 207.30, 36.99, 36.09, 29.87.

Example 20

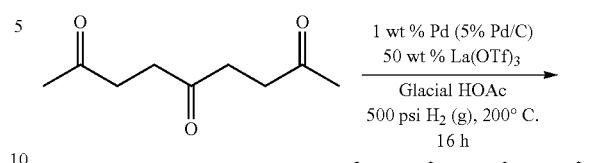

Nona-2,5,7-trione (170 mg, 1.00 mmol) was dissolved in glacial acetic acid (5 mL) and added along with Pd (170 mg of 10 wt % Pd/C, 0.160 mmol Pd, 16 mol % Pd relative to substrate) and La(OTf)$_3$ (170 mg, 0.290 mmol) to a stainless steel Swagelok equipped sample tube. The tube was then pressurized with 100 psi H$_2$ and heated to 225° C. for 14 hours. Upon cooling, the pressure was released and reaction mixture extracted from the vessel with methylene chloride (2×2 mL) and water (2×2 mL). The combined layers were filtered and the organic layer separated, dried over NaSO$_4$ and solvent removed in vacuo to yield n-nonane as a colorless oil (110 mg, 87%).

Nona-2,5,7-trione (170 mg, 1.00 mmol) was dissolved in 1M HOTf (5 mL) and added along with Pd/C (170 mg of 10 wt % Pd/C, 0.160 mmol Pd, 16 mol % Pd relative to substrate) and La(OTf)$_3$ (170 mg, 0.29 mmol) to a stainless steel Swagelok equipped sample tube. The tube was then pressurized with 100 psi H$_2$ and heated to 225° C. for 14 hours. Upon cooling, the pressure was released and reaction mixture extracted from the vessel with methylene chloride (2×2 mL) and water (2×2 mL). The combined layers were filtered and the organic layer separated, dried over NaSO$_4$ and solvent removed in vacuo to yield nonane as a colorless oil.

Nona-2,5,7-trione (170 mg, 1.00 mmol) was dissolved in 0.1M HOTf (5 mL) and added along with Pd/C (170 mg of 10 wt % Pd/C, 0.160 mmol Pd, 16 mol % Pd relative to substrate) and La(OTf)$_3$ (170 mg, 0.290 mmol) to a stainless steel Swagelok sample tube. The tube was then pressurized with 100 psi H$_2$ and heated to 225° C. for 14 hours. Upon cooling, the pressure was released and reaction mixture extracted from the vessel with methylene chloride (2×2 mL) and water (2×2 mL). The combined layers were filtered and the organic layer separated, dried over NaSO$_4$ and solvent removed in vacuo to yield nonane as a colorless oil.

Nona-2,5,7-trione (170 mg, 1.00 mmol) was dissolved in 1M HCl (5 mL) and added along with Pd/C (170 mg of 10 wt % Pd/C, 0.160 mmol Pd, 16 mol % Pd relative to substrate) and La(OTf)$_3$ (170 mg, 0.290 mmol) to a stainless steel Swagelok sample tube. The tube was then pressurized with 100 psi H$_2$ and heated to 225° C. for 14 hours. Upon cooling, the pressure was released and reaction mixture extracted from the vessel with methylene chloride (2×2 mL) and water (2×2 mL). The combined layers were filtered and the organic layer separated, dried over NaSO$_4$ and solvent removed in vacuo to yield nonane as a colorless oil.

Nona-2,5,7-trione (170 mg, 1.00 mmol) was dissolved in glacial acetic acid (5 mL) and added along with Pd/C (170 mg of 10 wt % Pd/C, 0.160 mmol Pd, 16 mol % Pd relative to substrate) and Fe(OTf)$_3$ (170 mg, 0.480 mmol) to a stainless steel Swagelok sample tube. The tube was then pressurized with 100 psi H$_2$ and heated to 225° C. for 14 hours. Upon cooling, the pressure was released and reaction mixture extracted from the vessel with methylene chloride (2×2 mL) and water (2×2 mL). The combined layers were filtered and the organic layer separated, dried over NaSO$_4$ and solvent removed in vacuo to yield nonane as a colorless oil as confirmed by GC-MS. $^1$H NMR (400 MHz, CDCl$_3$) δ 1.29 (m, 14H), 0.88 (s, 6H). $^{13}$C NMR (101 MHz, CDCl$_3$) δ 32.14, 29.73, 29.57, 22.81, 14.23.

Example 21

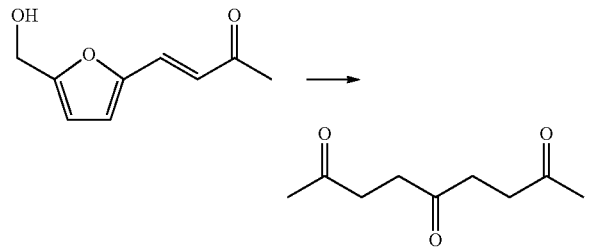

Unsaturated C$_9$ precursor (830 mg, 5.00 mmol) was dissolved in a 50% v/v solution of acetic acid in H$_2$O (15 mL) and Pd/C added (83 mg of 10 wt % Pd/C, 0.08 mmol Pd, 1.6 mol % Pd relative to substrate). The solution was added to a round bottom flask and put under an atmosphere of H$_2$ and heated at 60° C. for 1 hour to yield saturated C$_9$ in situ. The flask was then equipped with a condenser, opened to the air and heated at 100° C. for 3 hours to yield a colorless solution. The aqueous layer was neutralized with NaHCO$_3$ and extracted with dichloromethane (3×5 mL), dried over MgSO$_4$, filtered and solvent removed in vacuo to yield nona-2,5,7-trione (817 mg, 96% yield).

What is claimed:

1. A compound of formula I:

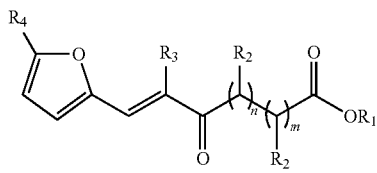

wherein
R$_1$ is H or C$_{1-6}$alkyl;
each R$_2$ is independently hydrogen or C$_{1-6}$alkyl;
R$_3$ is H or C$_{1-6}$alkyl;
R$_4$ is C$_{1-6}$alkyl or substituted C$_{1-6}$alkyl;
n is 1, 2, 3, or 4; and
m is 1, 2, 3, or 4.

2. The compound of claim 1, wherein R$_1$ is H.
3. The compound of claim 1, wherein R$_1$ is methyl or ethyl.
4. The compound of claim 1, wherein each R$_2$ is hydrogen.
5. The compound of claim 1, wherein R$_4$ is substituted C$_{1-6}$alkyl.
6. The compound of claim 5, wherein R$_4$ is —CH$_2$—OH.
7. The compound of claim 1, wherein R$_1$ is C$_{1-3}$ alkyl.
8. The compound of claim 1, wherein R$_1$ is C$_{1-4}$ alkyl.
9. The compound of claim 1, wherein R$_2$ is C$_{1-4}$ alkyl.
10. The compound of claim 1, wherein R$_2$ is C$_{1-3}$ alkyl.
11. The compound of claim 1, wherein R$_2$ is C$_{1-2}$ alkyl.
12. The compound of claim 1, wherein R$_2$ is methyl.
13. The compound of claim 1, wherein R$_4$ is C$_{1-4}$ alkyl or substituted C$_{1-4}$ alkyl.
14. The compound of claim 1, wherein R$_4$ is C$_{1-3}$ alkyl or substituted C$_{1-3}$ alkyl.
15. The compound of claim 1, wherein R$_4$ is C$_{1-2}$ alkyl or substituted C$_{1-2}$ alkyl.
16. The compound of claim 1, wherein R$_4$ is methyl or substituted methyl.
17. The compound of claim 5, wherein R$_4$ is C$_{1-6}$ alkyl substituted with —OH.
18. The compound of claim 17, wherein R$_4$ is —CH$_2$—OH or —CH$_2$—CH$_2$—OH.
19. The compound of claim 5, wherein R$_4$ is C$_{1-6}$ alkyl substituted with oxo or —COOH.
20. A compound of formula I:

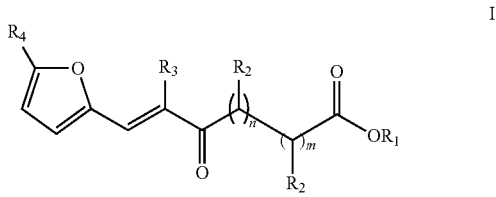

wherein:
R$_1$ is H or C$_{1-6}$ alkyl;
each R$_2$ is independently hydrogen or C$_{1-6}$ alkyl;
R$_3$ is H or C$_{1-6}$ alkyl;
R$_4$ is H, C$_{1-6}$ alkyl, or substituted C$_{1-6}$ alkyl;
n is 2, 3, or 4; and
m is 1, 2, 3, or 4,
with the proviso that when R$_1$ is H, R$_4$ is C$_{1-6}$ alkyl or substituted C$_{1-6}$ alkyl.

21. The compound of claim 20, wherein R$_1$ is H.
22. The compound of claim 20, wherein R$_1$ is methyl or ethyl.
23. The compound of claim 20, wherein R$_1$ is C$_{1-3}$ alkyl.
24. The compound of claim 20, wherein R$_1$ is C$_{1-4}$ alkyl.
25. The compound of claim 20, wherein each R$_2$ is hydrogen.
26. The compound of claim 20, wherein R$_2$ is C$_{1-4}$ alkyl.
27. The compound of claim 20, wherein R$_2$ is C$_{1-3}$ alkyl.
28. The compound of claim 20, wherein R$_2$ is C$_{1-2}$ alkyl.
29. The compound of claim 20, wherein R$_2$ is methyl.
30. The compound of claim 20, wherein R$_4$ is hydrogen.
31. The compound of claim 20, wherein R$_4$ is substituted C$_{1-6}$ alkyl.
32. The compound of claim 20, wherein R$_4$ is C$_{1-6}$ alkyl substituted with —OH.
33. The compound of claim 32, wherein R$_4$ is —CH$_2$—OH or —CH$_2$—CH$_2$—OH.
34. The compound of claim 20, wherein R$_4$ is C$_{1-4}$ alkyl or substituted C$_{1-4}$ alkyl.
35. The compound of claim 20, wherein R$_4$ is C$_{1-3}$ alkyl or substituted C$_{1-3}$ alkyl.
36. The compound of claim 20, wherein R$_4$ is C$_{1-2}$ alkyl or substituted C$_{1-2}$ alkyl.
37. The compound of claim 20, wherein R$_4$ is methyl or substituted methyl.
38. The compound of claim 31, wherein R$_4$ is C$_{1-6}$ alkyl substituted with oxo or —COOH.

* * * * *